United States Patent [19]

Dessau

[11] Patent Number: 4,469,913
[45] Date of Patent: Sep. 4, 1984

[54] SELECTIVE SORPTION OF LINEAR FUSED POLYNUCLEAR AROMATIC COMPOUNDS BY ZEOLITES

[75] Inventor: Ralph M. Dessau, Edison, N.J.

[73] Assignee: Mobil Oil Corporation, New York, N.Y.

[21] Appl. No.: 501,335

[22] Filed: Jun. 6, 1983

Related U.S. Application Data

[63] Continuation-in-part of Ser. No. 307,048, Sep. 20, 1981, Pat. No. 4,444,986, which is a continuation-in-part of Ser. No. 105,190, Dec. 19, 1979, Pat. No. 4,309,281.

[51] Int. Cl.$^3$ ................................................ C07C 7/13
[52] U.S. Cl. ................................. 585/828; 208/310 Z; 585/820; 585/826; 585/829
[58] Field of Search .............. 585/828, 820, 823, 824, 585/825, 826, 827, 829, 831; 208/310 Z

[56] References Cited

U.S. PATENT DOCUMENTS

| 3,699,182 | 10/1972 | Cattanach | 585/831 |
| 4,309,281 | 1/1982 | Dessau | 208/310 Z |
| 4,423,280 | 12/1983 | Dessau | 585/829 |

FOREIGN PATENT DOCUMENTS

| 652165 | 9/1975 | U.S.S.R. | 585/820 |
| 701983 | 8/1977 | U.S.S.R. | 585/820 |

*Primary Examiner*—Delbert E. Gantz
*Assistant Examiner*—A. Pal
*Attorney, Agent, or Firm*—A. J. McKillop; M. G. Gilman; L. G. Wise

[57] ABSTRACT

An improved technique for sorption of certain members of a ZSM-5 type of zeolites is provided. The class of zeolites is characterized by a silica to alumina mole ratio greater than 12 and a Constraint Index within the approximate range of greater than about 2 to about 12. The process of this invention involves sorption and/or selective separation of bicyclic fused-ring aromatic compounds, having a critical dimension less than 6.8 Angstrom units.

14 Claims, No Drawings

SELECTIVE SORPTION OF LINEAR FUSED POLYNUCLEAR AROMATIC COMPOUNDS BY ZEOLITES

CROSS-REFERENCE TO RELATED APPLICATION

This is a continuation-in-part of U.S. patent application Ser. No. 307,048 filed Sept. 20, 1981, now U.S. Pat. No. 4,444,986 which is a continuation in part of application Ser. No. 105,190, filed Dec. 19, 1979, now U.S. Pat. No. 4,309,281.

BACKGROUND OF THE INVENTION

1. Field of the Invention

This invention relates to a sorptive separation process using crystalline zeolites. More specifically, the invention pertains to the selective separation of certain bicyclic aromatic organic compounds in admixture with other organic compounds over a particular crystalline zeolite which selectively sorbs at least one of the compounds from the mixture. The zeolites found to be useful in the present process are those having a silica/alumina mole ratio of greater than about 12, a Constraint Index of between about greater than 2 and about 12, and in particular zeolites ZSM-5, ZSM-11, ZSM-23 and ZSM-35.

2. Description of the Prior Art

It has long been known that certain porous substances such as silica gel, activated char, and zeolites, have certain selective adsorption characteristics useful in resolving a hydrocarbon mixture into its component parts. Thus, silica gel is selective in removing aromatic hydrocarbons from non-aromatic hydrocarbons and activated chars are useful in separating olefins from mixtures with paraffins. Similarly, it is well known in the art that certain crystalline zeolites can be used to separate certain hydrocarbons from feed mixtures.

U.S. Pat. No. 3,724,170 discloses chromatographic separation of $C_8$ aromatic mixtures over zeolite ZSM-5. U.S. Pat. No. 3,699,182 to Cattanach discloses use of zeolite ZSM-5 in a process for selective separation of biphenyls from mixtures containing same and para-disubstituted aromatic isomers from mixtures containing same. Cattanach teaches a "keyhole selective sorption process wherein para-disubstituted aromatics may be selected from ortho-and/or meta-disubstituted aromatics," and also teaches that polycyclic aromatics are not sorbed by ZSM-5 type zeolites. British Pat. No. 1,420,796 shows use of zeolite ZSM-5 for adsorptive separation of p-xylene and ethylbenzene from a mixture comprised of the xylene isomers and ethylbenzene.

The ZSM-5 class of crystalline zeolites has been shown to be catalytically selective. This shape selectively can be further enhanced by the use of very large crystals, impregnation with Mg and P to reduce zeolite pore openings and coke selectivation. These modified zeolite catalysts have been very effective in such reactions as selective toluene disproportionation which yields predominantly paraxylene as the product and toluene-ethylene alkylation yielding primarily para-ethyltoluene.

Zeolite ZSM-5 possesses pore openings intermediate in size between the small pore and the large pore zeolites. It sorbs at room temperature straight chain mono-methyl-substituted paraffins and monocyclic hydrocarbons at significantly faster rates than those containing dimethyl-substituted or quaternary carbon atoms, and it excludes molecules with critical dimensions larger than that of 1,3,5-trimethylbenzene. Zeolite ZSM-5 has a pore system which differentiates catalytically molecules having a straight chain, a methyl substitution and a dimethyl substitution. The catalytic properties of ZSM-5 are further elucidated by Chen and Garwood in *Some Catalytic Properties of ZSM-5, a New Shape Selective Zeolite*, JOURNAL OF CATALYSIS, Vol. 52, No. 3 (May 1978).

Satterfield and Cheng, *Liquid Sorption Equilibrium of Selected Binary Hydrocarbon Systems in Type Y Zeolites*, AICHE JOURNAL, Vol. 18, No. 4, p. 720, July 1972 and Satterfield and Smeets, *Liquid Sorption Equilibria of Selected Binary Paraffin Systems in NaY Zeolite*, AICHE JOURNAL, Vol. 20, No. 3, p. 618, May 1974, teach that on zeolite Y aromatic compounds are selectively adsorbed over paraffins and smaller compounds are adsorbed in preference to larger compounds. Contrary to said teaching, the zeolites for use in the instant invention yield the unexpected results of selective adsorption of paraffins over aromatics and selective adsorption of higher molecular weight molecules over smaller members of the same family.

SUMMARY OF THE INVENTION

It has been discovered that linear fused polynuclear aromatic compounds having a critical dimension less than about 6.8 Angstrom Units can be sorbed by certain zeolites, such as ZSM-5. Naphthalene and other aromatic compounds having two fused adjacent rings, may be sorbed selectively from non-linear polycyclic organic compounds in admixture and from peri-substituted naphthalenes or the like, which have a critical dimension greater than about 6.8 Å. The particular zeolites useful in separation processes are characterized by a silica to alumina mole ratio of at least 12 and a Constraint Index within the approximate range of greater than 2 to about 12. In particular, said zeolites include ZSM-5, ZSM-11, ZSM-23 and ZSM-35, in acid form or cation-exchanged.

DESCRIPTION OF SPECIFIC EMBODIMENTS

The process of this invention is concerned with sorption and separation of organic compound mixtures by the selective sorption properties of certain zeolites.

The zeolites useful herein possess the ability to selectively sorb higher molecular weight organic compounds from mixtures thereof with lower molecular weight organic compounds within a homologous series. For instance, $\beta$-alkyl naphthalenes with n-alkyl substituents may be chromagraphically isolated or separated selectively. Isomeric mixtures can be fractionated, especially wherein a substantially non-sorbed peri-substituted compound, such as 1-methylnaphthalene is present in admixture with another fused-ring polycyclic aromatic compound having a critical dimension less than 6.8 A (e.g.-naphthalene or 2-methyl naphthalene). The homologous series from which compounds may selectively sorbed by the present process include polynuclear aromatic compounds, aralkyl or alkyl-substituted aromatic compounds and heteroatom-substituted compounds. The heteroatom substituents include halogen (e.g. F, Cl, Br and I), sulfur-containing groups (e.g. thiols, disulfides, thioacids and thioesters), oxygen-containing groups (e.g. ethers, alcohols, ketones, esters, aldehydes and acids), and nitrogen-containing groups (e.g. amines, imines, nitriles and amides) and polynuclear phenols.

Non-limiting examples of the process of this invention include sorption and/or selective separation of naphthalene, beta-substituted naphthalenes and certain 2, 3 or terminally-symmetrical substituted polynuclear aromatic compounds.

A limiting factor on which compounds will be sorbed to any extent, either selectively from a mixture or individually, by the zeolites for use herein is the critical dimension of the compound. For the zeolites herein utilized, the compounds must have a critical dimension of 6.8 Angstrom Units or less to be sorbed. In certain selective sorption process herein, both or all components of the mixture will have a critical dimension of less than 6.8 Angstroms. The technique is particularly advantageous in selective sorption of one or more components from various hydrocarbon mixtures in the presence of zeolite HZSM-5. The ability of a particular zeolite to selectively sorb one compound in admixture with another is characterized by deriving the "selectivity".

In adsorptive separation processes, an important factor that is used to determine the ability of a particular adsorbent to separate components of a feed mixture is the selectivity of the adsorbent for one component as compared to another component. The selectivity, as used throughout this specification, is defined as the ratio of the two components of the adsorbed or retained phase over the ratio of the same two components in the unadsorbed phase at equilibrium conditions. Selectivity is derived as follows:

$$\text{Selectivity} = S_{A,B} = \frac{(A \text{ adsorbed on zeolite})}{(B \text{ in solution})} \times \frac{(B \text{ adsorbed on zeolite})}{(A \text{ in solution})}$$

where A and B are the two components of the feed represented in volume percentages.

The equilibrium conditions as defined herein are determined when the feed is contacted with a bed of adsorbent and no change in composition results after such contacting. In other words, there is no net transfer of material occurring between the unadsorbed and adsorbed phases.

As can be seen, where the selectivity of the two components approaches unity, there is no preferential adsorption of one component by the adsorbent because the ratio of the feed to the components in the adsorbed and unadsorbed phases is equal. As the value of $S_{A,B}$ becomes less or greater than unity, there is a preferential selectivity by the adsorbent for one of the two components. When comparing a selectivity of component A over component B, an $S_{A,B}$ larger than unity indicates preferential adsorption of component A within the adsorbent, while an $S_{A,B}$ less than unity would indicate that component B is preferentially adsorbed by the adsorbent.

The novel process of the instant invention involves contacting a mixture, existing either as a gas, liquid or mixed fluid phase with a member of the class of zeolites of this invention for a period of time to selectively sorb a preferred compound within the internal pore structure of said zeolite. The components of the mixture that are not sorbed are thus carried off. The compound sorbed is thereafter recovered from the internal pore structure of the zeolite by conventional desorbing techniques such as stripping. Although inert solvents are employed in static batch systems to carry out many of the experiments illustrating this invention, the novel process of this invention can also be conducted in kinetic flow type (continuous) systems, e.g. continuous chromatographic type operation. In such a flow type system, a mixture is passed through a bed containing a member of the class of zeolites of the present invention. The preferred compound is adsorbed or retained in the bed, while the unadsorbed compound is removed. The processes of this invention can be conducted in the presence of polar, e.g. water or alcohol, or non-polar solvents. Thus, selective sorptions of the kind and type described herein can take place in the presence of water, i.e. in aqueous solution.

The temperature at which the novel process of this invention is conducted is not considered critical, so long as it is maintained below that required for chemical reaction to occur, e.g. below cracking temperature. The temperature should thus be maintained below about 150° C. when an acidic zeolite is used (e.g. a zeolite having an Alpha value greater than 10). When a relatively non-acidic zeolite is used (e.g. one having a $SiO_2/Al_2O_3$ mole ratio of about 1000 or more, for instance) or when the zeolite has been converted to the alkali metal-containing form, e.g. Na, by ion exchange, for instance, then higher temperatures may be used, such as up to about 400° C. Preferably, the processes of this invention can be conducted in the temperature range between ambient and about 150° C.

Obtaining even higher selectivities for the zeolites for this improved process can be accomplished by reducing the diffusional rate characterics of these zeolites. The diffusional rate characteristic is defined as the rate of which a zeolite, or other adsorbent, sorbs a particular hydrocarbon, e.g. hexane or o-xylene. Modification of the diffusional rate characteristics may be suitably effected by precoking. Another means of achieving desired lower diffusional rate characteristics is the use of large crystal size zeolite having a minimum crystal dimension of greater than about 0.5 micron. Generally, the crystal size should be in the approximate range of between about 0.5 micron and greater than about 250 microns, and preferably in the range of between about 0.5 micron and 250 microns. As used throughout this specification and claims, zeolites with crystal diameters of about 0.02 micron to about 0.5 micron will be designated as "small crystal size" and zeolites with crystal diameters greater than about 0.5 micron will be designated as "large crystal size".

Still another means of achieving desired lower diffusional rate characteristics is to incorporate, such as by cation exchange, bulky cations such as cesium or tetramethylammonium cations with the useful zeolites of this invention. Other cations which may be exchanged into the zeolite to affect lower diffusional rate characteristics and thereby increase selectivity thereof for the present process include $Na^+$, $H^+$, $Cu^{++}$, $K^+$, $Sr^{++}$ and similar cations. A correlation of sorption selectivity exhibited by the exchanged zeolite for use herein with the ionic radius of the cation involved may be demonstrated.

Silica/alumina mole ratio also has an effect on the sorption selectivity of the zeolites for use herein, especially where large polarity differences are involved. Thus, for example, H-ZSM-5 having a $SiO_2/Al_2O_3$ mole ratio of 1670 may have a selectivity from four to five times that of a H-ZSM-5 having a $SiO_2/Al_2O_3$ mole ratio of 75. Likewise, it has been found that steaming a zeolite useful herein will also increase selectivity thereof. For example, an unsteamed H-ZSM-5 may provide a selectivity factor of 3.2, while that same zeolite after having been steamed for 2 hours at 538° C. will provide a selectivity of as much as 7.3.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is valuable in some instances to use zeolites having much higher silica to alumina mole ratios, e.g. 1600 and above. In addition, zeolites as otherwise characterized herein but which are substantially free of aluminum, i.e. having silica to alumina mole ratios up to and including infinity, are found to be useful and even preferable in some instances. Such "high silica" or "highly siliceous" zeolites are intended to be included within this description. Also to be included in this definition are the pure silica analogs of the useful zeolites of this invention, i.e. having absolutely no aluminum (silica to alumina mole ratio of infinity). Thus zeolites useful herein have silica to alumina mole ratios of between about 12 and infinity, preferably greater than 200, more preferably greater than 500 and even more preferably greater than 1000. The ZSM-5 type zeolites may contain in addition to silica the oxides of B, Cr, Fe or Ga.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules, i.e. those having a critical dimension of greater than 6.8 Angstrom Units. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of a particular zeolite solely from theoretical structural considerations.

Rather than attempt to judge from crystal structure whether or not a zeolite possesses the necessary constrained access to molecules or larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

There also may be instances where the activity is so low (i.e. silica to alumina mole ratio approaching infinity) that the constraint index cannot be adequately measured, if at all. In such situations, Constraint Index is meant to mean the Constraint Index of the exact same substance (i.e. same crystal structure as determined by such means as x-ray diffraction pattern) but in a measureable form (i.e. aluminum containing form).

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Constraint Index values for some typical materials are:

|  | CONSTRAINT INDEX |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may effect the constraint index. Therefore, it will be appreciated that it may be possible to so select test conditions as to establish more than one value in the range of greater than about 2 to about 12 for the Constraint Index of a particular zeolite. Such a zeolite exhibits the constrained access as herein defined and is to be regarded as having a Constraint Index in the range of greater than about 2 to about 12. Also contemplated herein as having a Constraint Index in the range of greater than about 2 to about 12 and therefore within the scope of the defined novel class of highly siliceous zeolites are those zeolites which, when tested under two or more sets of conditions within the above-specified ranges of temperature and conversion, produce a value of the Constraint Index slightly less than 2, e.g. 1.9, or somewhat greater than 12, e.g. 14 or 15, with at least one other value within the range of greater than about 2 to about 12. Thus, it should be understood that the Constraint Index value as used herein is an inclusive rather than an exclusive value. That is, a crystalline zeolite when identified by any combination of conditions within the testing definition set forth herein as having a Constraint Index in the range of greater than about 2 to 12 is intended to be included in the instant novel zeolite definition whether or not the same identical zeolite, when tested under other of the defined conditions, may give a Constraint Index value outside of the range of greater than about 2 to about 12.

The novel class of zeolites defined for use herein is exemplified by ZSM-5, ZSM-11, ZSM-23 and ZSM-35.

ZSM-5 is described in greater detail in U.S. Pat. No. 3,702,886 and Re. No. 29,948. The entire descriptions contained within those patents, particularly the X-ray diffraction pattern of therein disclosed ZSM-5, is incorporated herein by reference.

ZSM-11 is described in U.S. Pat. No. 3,709,979. That description, and in particular the X-ray diffraction pattern of said ZSM-11, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are unsuitable for use herein, possibly because the intra-crystalline free space is occupied by organic cations from the forming solution. They may be made suitable by calcination in an inert atmosphere, such as, for example, at about 538° C. for from about one hour to about 5 hours in a nitrogen or air atmosphere. If desired these zeolites may be base exchanged with suitable compounds, e.g. salts, to get desired cationic form, e.g. sodium, hydrogen, ammonium, etc. The presence of organic cations in the forming solution may not be absolutely essential to the formation of this type zeolite; however, the presence of these cations does appear to favor the formation of this special class of zeolite.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-23 and ZSM-35, with ZSM-5 being particularly preferred.

In a preferred aspect of this invention, the zeolites hereof are selected as those providing, among other things, a crystal framework density in the dry hydrogen form of not less than about 1.6 grams per cubic centimeter. It has been found that zeolites which satisfy all three of the discussed criteria are most desired for several reasons. Therefore, the preferred zeolites useful with respect to this invention are those having a Constraint Index as defined above of greater than about 2 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intrqcrystalline free space.

It is possible that the unusual sustained activity and stability of this special class of zeolites is associated with its high crystal anionic framework density of not less than about 1.6 grams per cubic centimeter. This high density must necessarily be associated with a relatively small mount of free space within the crystal, which might be expected to result in more stable structures. This free space, however, is important as the focus of catalytic activity.

Crystal framework densities of some typical zeolites, including some which are not within the purview of this invention are:

|  | Void Volume | Framework Density |
|---|---|---|
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

The following examples will serve to illustrate the process of the invention without limiting same.

EXAMPLE 1

This example illustrates the preparation of small crystal size ZSM-5.

An organic salt solution was prepared by mixing 1.6 parts of n-propyl bromide, 1.9 parts of tri-n-propylamine, 3.1 parts of methyl ethyl ketone and 10.4 parts of water. The mixture was reacted at about 100° C. for about 14 hours. The aqueous phase of the reacted mixture is designated Solution A.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace). The solution was cooled to approximately 15° C.

An acid solution was prepared by adding 1 part aluminum sulfate (17.2 wt % $Al_2O_3$) to 16.4 parts water followed by 2.4 parts NaCl and 2.9 parts of Solution A.

These solutions were mixed in an agitated vessel while 3.9 parts of NaCl were added. The gel molar ratios expressed as oxides are the following.

$SiO_2/Al_2O_3 = 78.4$
$Na_2O/Al_2O_3 = 49.9$

The gel was agitated for 4 hours at ambient temperature then heated to 95°-110° C. and held for 40 hours with severe agitation. When approximately 65% of the gel was crystallized, the temperature was increased to 150°-160° C. and held there until crystallization was complete.

The zeolite slurry product was diluted with 4-5 parts water per part slurry and 0.0002 parts of flocculent (Rohm & Haas Primafloc C-7) per part slurry, allowed to settle and supernatant liquid was drawn off. The settled solids were reslurried to the original volume of the preceding step with water and 0.00005 parts of flocculent per part slurry. After settling, the aqueous phase was decanted. This procedure was repeated until the sodium level of the zeolite was less than 1.0 wt %. The washed zeolite was then filtered, dried and identified as ZSM-5 having a silica/alumina mole ratio of at least 12; i.e., about 70, and a Constraint Index of about 8.3.

The dried zeolite product was calcined in flowing $N_2$ for 3 hours at 538° C. than ion exchanged twice with 1N $NH_4NO_3$ solution (5 parts $NH_4NO_3$ solution/1 part zeolite) for 1 hour at ambient temperature and dried at about 120° C. to arrive at a $NH_4$-ZSM-5 zeolite.

EXAMPLE 2

The preparation of the acid form (HZSM-5) of the small crystal size $NH_4$-ZSM-5 of Example 1 was conducted via the programmed calcination of the $NH_4$-ZSM-5 of Example 1 with air in a furnace at the approximate range of about 1.1° C./minute until a temperature of 537.8° C. was obtained and maintained at that temperature for 5 hours.

EXAMPLE 3

This example illustrates the preparation of large crystal size ZSM-5.

A sodium silicate solution was prepared by mixing 16 parts water and 27.7 parts sodium silicate (28.7 wt % $SiO_2$, 8.9 wt % $Na_2O$, 62.4% $H_2O$) followed by addition of 0.08 parts Daxad 27 (W. R. Grace). The solution was cooled to approximately 15° C.

An acid solution was prepared by adding 1 part aluminum sulfate (17.2 wt % $Al_2O_3$) to 16.4 parts water followed by 2.4 parts sulfuric acid (93 wt % $H_2SO_4$) and 1.2 parts NaCl.

These solutions were mixed in an agitated vessel while 3.9 parts of NaCl were added. The gel molar ratios expressed as oxides are the following:

$SiO_2/Al_2O_3 = 78.4$
$Na_2O/Al_2O_3 = 49.9$

An organic solution was prepared by adding 1.6 parts n-propyl bromide and 3.1 parts methyl ethyl ketone to 1.9 parts tri-n-propylamine and added to the gel.

The mixture was reacted at 65.5°–71.1° C. with severe agitation for 29 hours.

The zeolite slurry product was diluted with 4–5 parts water per part slurry and 0.002 parts of flocculent (Rohm & Haas Primafloc C-7) per part slurry, allowed to settle and supernatant liquid was drawn off. The settled solids were reslurried to the original volume of the preceding step with water and 0.0005 parts of flocculent per part slurry. After settling, the aqueous phase was decanted. This procedure was repeated until the decant supernatant liquid was Cl-free. The washed zeolite was then filtered, dried and identified as ZSM-5 having a silica/alumina mole ratio of at least 12; i.e., about 70, and a Constraint Index of about 8.3.

The dried zeolite product was calcined in flowing $N_2$ for 3 hours at 538° C. then ion exchanged twice with 1N $NH_4NO_3$ solution (5 parts $NH_4NO_3$ solution/1 part zeolite) for 1 hour at ambient temperature and dried at about 120° C. to arrive at a $NH_4$-ZSM-5 zeolite.

EXAMPLE 4

The preparation of the acid form (HZSM-5) of the large crystal size $NH_4$-ZSM-5 of Example 3 was conducted via the programmed calcination of $NH_4$-ZSM-5 of Example 3 with air in a furnace at the rate of about 1.1° C./minute until a temperature of 537.8° C. was attained and maintained at that temperature for 5 hours.

EXAMPLE 5

This example illustrates the preparation of small crystal size ZSM-11.

A sodium silicate solution was prepared by mixing 16.8 parts water, 28.9 parts sodium silicate (28.7 wt % $SiO_2$, 8.9 wt % $Na_2O$, 62.4 wt % $H_2O$) 0.05 parts 50% wt NaOH and 0.08 parts Daxad 27 (W. R. Grace).

An acid solution was prepared by adding 1 part aluminum sulfate (17.2% wt $Al_2O_3$) to 12.6 parts $H_2O$ and then adding 2.9 parts $H_2SO_4$ and 1.7 parts NaCl.

These solutions were mixed in an agitated vessel and 1.2 parts NaCl and 0.8 parts $H_2O$ were added to the gel.

An organic solution containing 2.9 parts tetrabutylammonium bromide and 4.2 parts water was then added to the gel and thoroughly blended.

The mixture was heated to 93.3° C. and held for 234 hours with a high level of agitation. At the end of this period the temperature was raised to 137.8° C. for 72 hours to complete crystallization.

The crystallized product was washed and dried and then identified as 105% crystallinity ZSM-11 by X-ray diffraction with the following chemical analysis:

| | % wt. |
|---|---|
| $Al_2O_3$ | 1.99 |
| $SiO_2$ | 92.0 |
| Na | 0.60 |
| N | 0.65 |

-continued

| | % wt. |
|---|---|
| C | 9.95 |

The washed and dried zeolite product was calcined in flowing $N_2$ for 3 hours at 537.8° C. then ion exchanged with 1N $NH_4NO_3$ solution (5 parts $NH_4NO_3$ solution/1 part zeolite) for 1 hour at ambient temperature and dried at about 121° C.

The silica to alumina mole ratio of the resultant zeolite was 78.

EXAMPLE 6

This example illustrates the preparation of small crystal size zeolite $NH_4$-ZSM-12.

A reaction mixture was prepared by mixing 65 parts of Hi-Sil (a precipitated $SiO_2$), 6.3 parts NaOH, 1 part $Al(NO_3)_3 \cdot 9H_2O$, 40 parts tetraethylammonium bromide and 310 parts $H_2O$. The mixture was charged to a vessel, thoroughly agitated and heated to about 160° C. and held for about 16 hours with agitation. At this point the reaction mixture was cooled and 1.1 parts of $NaAlO_2$ and 2.7 parts $H_2O$ were added. The reaction mixture was reheated to 160° C. and held for an additional 24 hours at 160° C. with agitation to complete crystallization.

The crystallized product was washed and dried and then identified as 90% ZSM-12 by X-ray diffraction with the following chemical analysis:

| | % wt. |
|---|---|
| $Al_2O_3$ | 1.79 |
| $SiO_2$ | 95.1 |
| Na | 0.34 |
| N | 0.98 |
| C | 7.63 |

The washed and dried zeolite was calcined in flowing $N_2$ for 3 hours at 537.8° C. then ion exchanged three times with 1N $NH_4NO_3$ solution (5 parts $NH_4NO_3$ solution/1 part zeolite) for 1 hour at ambient temperature and dried at about 121° C. to finally obtain a $NH_4$-ZSM-12 zeolite.

The silica to alumina mole ratio of the resultant zeolite was 95.

EXAMPLE 7

The preparation of HZSM-12 from the $NH_4$-ZSM-12 of Example 6 was conducted via the programmed calcination of $NH_4$-ZSM-12 with air in a furnace at the rate of about 1.1° C./minute until a temperature of 537.8° C. was attained and maintained at that temperature for 5 hours.

EXAMPLE 8

Small crystal size Cs-ZSM-5 was prepared by the ion-exchange of $NH_4$-ZSM-5 of Example 1 with a cesium chloride solution containing a small amount of cesium hydroxide, resulting in an ammonium removal of approximately 99%.

EXAMPLE 9

This example illustrates the preparation of a highly siliceous ZSM-5 zeolite with a silica to alumina mole ratio of about 1600 to 1.

Prereacted organics preparation

The following materials were charged to an autoclave: 0.30 parts methylethyl ketone, 0.18 parts tri-n-propylamine and 0.15 parts p-propyl bromide. The contents were mixed with gentle agitation for 15 minutes. The agitation was stopped and 1 part water was charged to the autoclave. The autoclave was sealed and heated to 104.4° C. and held at 104.4° C. for 15 hours. After this reaction period the temperature was raised to 160° C. and the unreacted organics were flashed off. The aqueous phase was removed containing the prereacted organics and contained 1.44% wt. nitrogen.

Zeolite Synthesis Solution Preparation

Silicate Solution
1 part Q-brand sodium silicate
0.58 parts $H_2O$
0.0029 parts Daxad 27

Acid Solution
0.10 parts $H_2SO_4$
0.045 parts NaCl
0.56 parts prereacted organics
0.16 parts $H_2O$ Additional Solids
0.14 parts NaCl Additional Liquid
0.029 parts $H_2O$

Procedure

The silicate solution and acid solution were mixed in a mixing nozzle to form a gel which was discharged into an autoclave to which 0.029 parts water had been previously added. The gel was whipped by agitation and 0.14 parts NaCl were added and thoroughly blended. The autoclave was sealed and heated to about 104.4° C. with agitation at 90 rpm and held for 54.3 hours until crystallization was complete. The contents of the autoclave were cooled and discharged. The crystallized product was analyzed by x-ray diffraction and was found to be 100 weight percent ZSM-5. The chemical analysis of the thoroughly washed crystalline product was as follows:

|       | % wt  | Mole Ratio |
|-------|-------|------------|
| $Al_2O_3$ | 0.10  | 1.0        |
| $SiO_2$   | 98.3  | 1670       |
| Na    | 1.6   | —          |
| $Na_2O$   | —     | 35.5       |
| N     | 0.75  | 63.9       |
| C     | 8.98  | 892        |

EXAMPLE 10

The preparation of HZSM-23 is conducted as in Examples 1 and 10 of U.S. Pat. No. 4,076,842, incorporated herein by reference. The HZSM-23 exhibits a $SiO_2/Al_2O_3$ mole ratio of 60.6, a sodium content of 0.05 weight percent, and a Constraint Index of 9.1.

EXAMPLE 11

The preparation of HZSM-35 is conducted as in Example 1 of U.S. Pat. No. 4,016,245, incorporated herein by reference, the zeolite product thereof being ion-exchanged and calcined as in Examples 1 and 2 of this application. The HZSM-35 exhibits a $SiO_2/Al_2O_3$ mole ratio of 29.9 and a Constraint Index of 4.5.

DIAGNOSTIC EVALUATIONS

In order to develop a meaningful diagnostic evaluation of zeolites that could be used for predicting separation properties, the selective sorption properties of various zeolites under competitive conditions are examined. In general, two or more substrates are dissolved in an inert (non-sorbable) solvent, i.e. one having a critical dimension greater than 6.8 Angstroms, and the relative decrease in concentration of each sorbate due to addition of various zeolites is measured.

The sorbates to be used are the purest forms available commercially and the inert non-soluble solvent to be used is 1,3,5-trimethylbenzene (mesitylene) or 1,3,5-triisopropylbenzene (TPB). In a typical experiment, 2 parts by weight of a solution containing two or more sorbates (2.5% by weight each) in the inert solvent is added directly to 1 part of a zeolite contained in a vial. This mixture, which is occasionally shaken or stirred at room temperature, is sampled periodically for changes in substrate concentrations. These samples are analyzed by vapor phase chromatography and are compared to the original solution analyzed in the identical manner. The selectivity is calculated by the formula defined hereinabove.

Several examples serve to illustrate the utility of the zeolites for use herein for preferentially sorbing a beta-substituted fused-ring polynuclear compound from its alpha-substituted aromatic isomer and heavier hydrocarbon compounds over lighter hydrocarbon compounds within a homologous series. The zeolite used was prepared as in Example 2 and the results of Examples 12–13, carried out in accordance with the above diagnostic procedure at room temperature (20°–25° C.) for a time of 2 hours.

EXAMPLE 12

Homologous linear paraffins, n-hexadecane and n-nonane are tested in mesitylene, as described above with 74 wt. % of the higher molecular weight hexadecane sorbed preferentially, as compared with 33 wt. % nonane. The total sorption is 71 mg/g of zeolite and the selectivity (A/B) is 5.7.

EXAMPLE 13

The standard experimental procedure of Example 12 is repeated with toluene (83 wt. %) being sorbed preferentially over benzene (68%). The total sorption of both compounds is 72 mg/g and selectivity is 2.3.

EXAMPLE 14

A solution is prepared containing 75 parts by weight of naphthalene, 125 parts of 1-methylnaphthalene ($\alpha$-isomer), 85 parts of 2-methylnaphthalene ($\beta$-isomer), 120 parts mesitylene and 3600 parts of 1,3,5-triisopropyl benzene solvent. Two parts by weight of solution was contacted with 1 part HZSM-5 zeolite according to Example 2 at room temperature (20°–25° C.) for 24 hours. The 2-methylnaphthalene compound was preferentially sorbed (70 wt. %) over naphthalene (40 wt. %) and its peri-substituted 1-methylnaphthalene isomer (nil).

Since the preferred bicyclic fused-ring aromatic compounds have a molecular weight greater than 128 and are usually solid at room temperature, it is preferred to sorb such compounds from solutions. However, vapor phase sorption may be feasible if the sorbed compound is sufficiently volatile. It is noted that higher molecular weight compounds are preferably sorbed over lower homologs, provided both homologs have a critical dimension less than 6.8 A. Thus, toluene is selectively sorbed over benzene despite the fact that benzene has a higher melting point (a property once believed to be most closely related to the crystal packing efficiency of a substrate).

The present discovery may be applied to a variety of bicyclic aromatic compounds, having at least two fused rings, such as a naphthalene moiety. The following structural formula demonstrates operative naphthalene class:

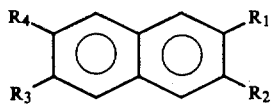

where one or more ring substituents $R_1$, $R_2$, $R_3$ or $R_4$ is selected from alkyl (preferably n-alkyl having 1 to 8 carbom atoms), heteroatom groups (alkyl ethers, acids and esters, hydroxyl-, cyano-) or cyclo-aliphatic radicals. Examples of sorbable compounds include 2-methyl naphthalene, methyl $\beta$-naphthyl ether, $\beta$-naphthol, $\beta$-naphthoic acid, and 2-cyano-naphthalene. Various 2, 3, 6 or 7-polysubstituted naphthalenes are within the inventive concept.

These compounds may be preferentially sorbed in mixture with other compatible organic compounds having a critical dimension greater than about 6.8 Angstroms, such as per-substituted compounds, (e.g., 1, 4, 5 or 8-substituted naphthalene and the like). Bicyclic naphthalene type compounds can be separated from non-linear isomers or homologous compounds.

Process conditions may be varied widely within the inventive concept. Ordinarily ambient temperature and pressure conditions are preferred; however, higher temperatures may be employed if the desired components are stable. Acid zeolites tend to decompose organic compounds above 150° C.; therefore, contact temperature is preferred in the range of about 20° C. to 150° C. Feed stock concentration, molecular weight and carbon content can also vary substantially within the operating parameters, with $C_{10}$ to $C_{20}$ compounds being preferred.

While the inventive concept has been described with reference to specific embodiments, there is no intent to limit the inventive concept except as set forth in the following claims.

What is claimed is:

1. A process for the selective separation of a bicyclic fused-ring polynuclear aromatic compound having a critical dimension less than 6.8 Angstrom units in admixture with another polynuclear compound having a critical dimension greater than 6.8 Angstrom units, which comprises contacting the mixture with a zeolite having a $SiO_2/Al_2O_3$ mole ratio of at least 12 and a Constraint Index of greater than 2 to about 12 to effect selective sorption of said bicyclic fused-ring polynuclear aromatic compound.

2. The process of claim 1 wherein said zeolite has been calcined in an inert atmosphere.

3. The process of claim 1 wherein said zeolite has had its original cations replaced, at least in part, by ion exchange with a cation selected from the group consisting of hydrogen, ammonium, tetramethylammonium, rare earth metals and metals of Groups I through VIII of the Periodic Table of Elements.

4. The process of claim 2 wherein said zeolite has after calcination had its original cations replaced, at least in part, by ion exchange with a cation selected from the group consisting of hydrogen, ammonium, tetramethylammonium, rare earth metals and metals of Groups I through VIII of the Periodic Table of Elements.

5. The process of claim 3 wherein said zeolite has after ion exchange been calcined in an inert atmosphere.

6. The process of claim 4 where said zeolite has after ion exchange been calcined in an inert atmosphere.

7. The process of claim 1, 2, 3, 4, 5 or 6 wherein said zeolite is comprised substantially of crystals of a size greater than about 0.5 micron.

8. The process of claim 3, 4, 5 or 6 wherein said replacing cation is cesium.

9. The process of claim 1, 2, 3, 4, 5 or 6 wherein the mixture is in the liquid phase.

10. The process of claim 1 wherein the zeolite is ZSM-5, ZSM-11, ZSM-23 or ZSM-35.

11. A process for the selective separation of 2-methyl-naphthalene in admixture with 1-methyl-naphthalene which comprises contacting the mixture with a zeolite characterized by a silica to alumina mole ratio of at least about 12 and a constraint index of greater than 2 to about 12, to effect the selective sorption of 2-methyl-naphthalene by said zeolite.

12. The process of claim 11 wherein said zeolite consists essentially of HZSM-5.

13. A process for the selective sorption of naphthalene or a beta-substituted naphthalene compound having a critical dimension less than 6.8 Angstrom units in solution with at least one other organic compound having a critical dimension greater than 6.8 Angstrom units selected from the group consisting of hydrocarbons and substituted hydrocarbons, which comprises contacting the mixture with zeolite, said zeolite characterized by a silica to alumina mole ratio of at least about 12, to effect the selective sorption of beta-naphthalene compound by said zeolite.

14. The process of claim 13 wherein the zeolite consists essentially of HZSM-5.

* * * * *